United States Patent [19]

Petersen et al.

[11] 4,336,369

[45] Jun. 22, 1982

[54] SELECTIVELY PROTECTED 1-N-(ω-AMINOALKOXYCARBONYL)-SISOMICIN DERIVATIVES

[75] Inventors: Uwe Petersen, Leverkusen; Eckart Voss, Cologne; Peter Stadler, Haan, all of Fed. Rep. of Germany

[73] Assignee: Bayer Aktiengesellschaft, Leverkusen, Fed. Rep. of Germany

[21] Appl. No.: 149,384

[22] Filed: May 13, 1980

[30] Foreign Application Priority Data

May 30, 1979 [DE] Fed. Rep. of Germany ....... 2921974

[51] Int. Cl.$^3$ ..................... C07H 15/22; A61K 31/71
[52] U.S. Cl. .................................. 536/13.9; 424/181
[58] Field of Search ................................ 536/17 R, 10

[56] References Cited

U.S. PATENT DOCUMENTS

| | | | |
|---|---|---|---|
| 4,008,218 | 2/1977 | Akita et al. | 536/17 R |
| 4,029,882 | 6/1977 | Wright | 536/17 R |
| 4,180,565 | 12/1978 | Mallams et al. | 536/17 R |
| 4,234,572 | 11/1980 | Petersen et al. | 536/17 R |

*Primary Examiner*—Blondel Hazel
*Attorney, Agent, or Firm*—Sprung, Horn, Kramer & Woods

[57] ABSTRACT

The invention relates to selectively protected 1-N-(ω-aminoalkoxycarbonyl)-sisomicin derivatives and methods for their procurement. Said derivatives are useful as intermediates for the procurement of highly active antibacterial agents of low toxicity.

3 Claims, No Drawings

SELECTIVELY PROTECTED 1-N-(ω-AMINOALKOXYCARBONYL)-SISOMICIN DERIVATIVES

The invention relates to new, selectively protected 1-N-(ω-aminoalkoxycarbonyl)-sisomicin derivatives, which are used as intermediate products for the preparation of highly active antibiotics, and to a process for the preparation of the selectively protected compounds.

The new compounds are represented by the formula (I)

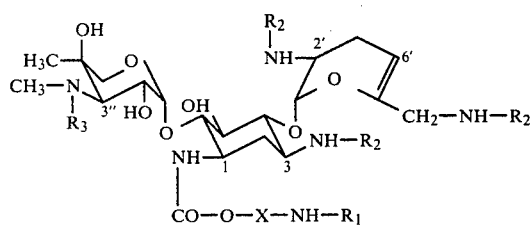

in which

X represents a straight-chain, branched or cyclic saturated or unsaturated aliphatic radical with 2 to 10 C atoms, $R_1$ represents hydrogen, $C_1$-$C_4$-alkyl or benzyl, $R_2$ represents CO-$R_4$ or S-$R_5$ and $R_3$ represents S-$R_5$, wherein $R_4$ denotes a radical of the formulae

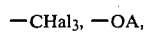

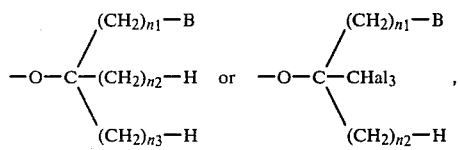

A denotes optionally substituted phenyl,

B denotes hydrogen or optionally substituted phenyl, $n_1$, $n_2$ and $n_3$ denote a number from 0 to 5, Hal denotes fluorine, chlorine or bromine and $R_5$ denotes optionally substituted phenyl or di- or tri-phenylmethyl.

In particular, X represents a $C_2$-$C_6$-alkylene radical and $R_1$ represents hydrogen.

Examples of suitable substituents of the optionally substituted phenyl or di- or tri-phenylmethyl radicals $R_5$ are 1 to 3 substituents from the series comprising trifluoromethyl, nitro, $C_1$-$C_4$-alkyl, $C_1$-$C_4$-alkoxy, $C_1$-$C_4$-alkoxycarbonyl and phenyl, or 1 to 5 halogen atoms, preferably chlorine atoms. Examples of —$SR_5$ groups which may be mentioned are o-nitrophenylsulphenyl and 2,4,5-trichlorophenylsulphenyl.

Suitable substituents of the optionally substituted phenyl radicals A and B are 1 or 2 substituents from the series comprising nitro, halogen, preferably chlorine, $C_1$-$C_4$-alkyl, $C_1$-$C_4$-alkoxy and phenyl.

The compounds of the formula I according to the invention are obtained by a process in which selctively protected sisomicin derivatives of the formula II

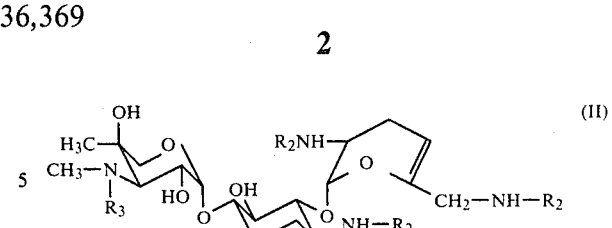

in which $R_2$ and $R_3$ have the meaning indicated above, are reacted with an acylating agent of the formula (III)

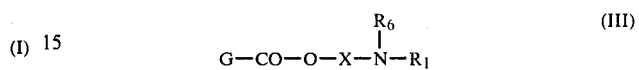

wherein

X and $R_1$ have the meaning indicated above,

G represents a leaving group, preferably halogen, such as chlorine or bromine, azido, optionally substituted phenoxy, such as 4-nitrophenoxy or 2,4,5-trichlorophenoxy, or a radical of the formula

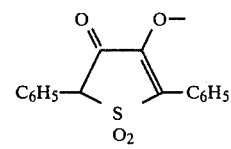

and $R_6$ represents CO—$R_4$ or S—$R_5$, wherein $R_4$ and $R_5$ have the meaning indicated above, with the condition that $R_6$ represents $COR_4$ if $R_2$ denotes $SR_5$ and $R_6$ represents $SR_5$ if $R_2$ denotes $COR_4$, if appropriate in the presence of a base, to give compounds of the formula (IV)

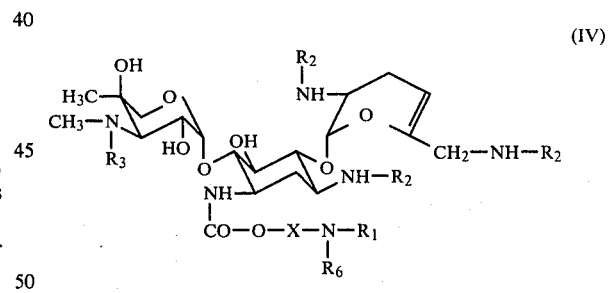

in which $R_1$, $R_2$, $R_3$, $R_6$ and X have the meaning indicated above, and the protective group $R_6$ is then split off selectively, in the presence of the protective groups $R_2$ and of $R_3$.

If 2′,3,3″,6′-tetra-N-(o-nitrophenylsulphenyl)sisomicin and 4-nitrophenyl 2-trifluoroacetylaminoethyl carbonate are used as starting substances, the course of the reaction can be represented by the following equation.

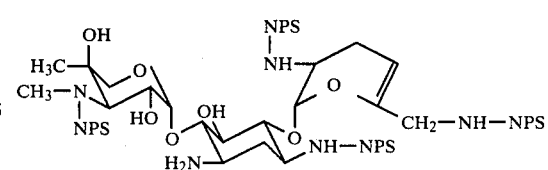

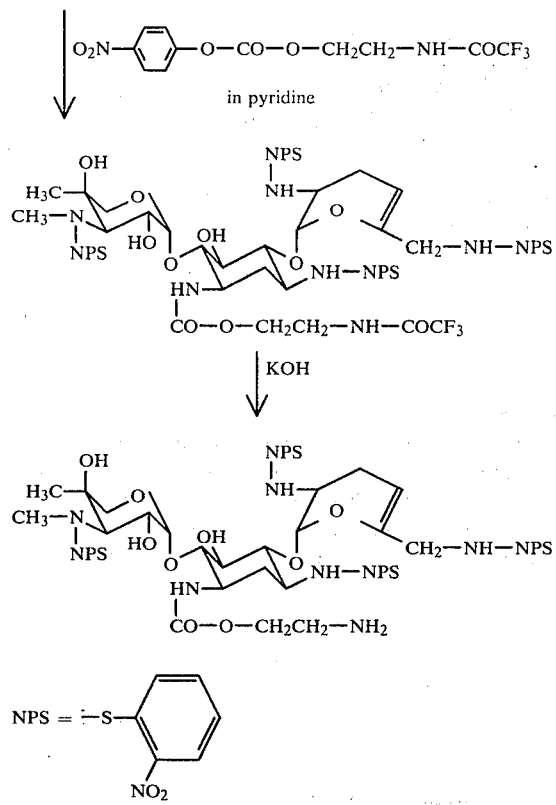

2′,3,3″,6′-Tetra-N-(o-nitrophenylsulphenyl)-sisomicin, 3″-N-(o-nitrophenylsulphenyl)-2′,3,6′-tris-N-trichloroacetyl-sisomicin, 3″-N-(o-nitrophenylsulphenyl)-2′,3,6′-tris-N-trifluoroacetyl-sisomicin, 3″-N-(o-nitrophenylsulphenyl)-2′,3,6′-tris-N-(2,2,2-trichloroethoxycarbonyl)-sisomicin, 3″-N-(o-nitrophenylsulphenyl)-2′,3,6′-tris-N-(1,1-dimethyl-2,2,2-trichloroethoxycarbonyl)-sisomicin, 3″-N-(o-nitrophenylsulphenyl)-2′,3,6′-tris-N-(4-methoxybenzyloxycarbonyl)-sisomicin, 3″-N-(o-nitrophenylsulphenyl)-2′,3,6′-tris-N-phenoxycarbonyl-sisomicin and 3″-N-(o-nitrophenylsulphenyl)-2′,3,6′-tris-N-(tert.-butoxycarbonyl)-sisomicin are preferably used as starting substances of the formula (II), and these compounds are prepared by the process described in DE-OS No. (German Published Specification) 2,726,197, corresponding to U.S. application Ser. No. 913,135 filed June 6, 1973 or via the following stages:

(1) reaction of penta-N-(o-nitrophenylsulphenyl)-sisomicin (German Offenlegungsschrift (German Published Specification) No. 2,726,197) with dimethyl-(1,2-dimethylpropyl)-silyl chloride to give penta-N-(o-nitrophenylsulphenyl)-2″-O-[dimethyl-(1,2-dimethylpropyl)-silyl]-sisomicin;

(2) splitting off of the o-nitrophenylsulphenyl groups from 2′-, 3- and 6′-N with 2-mercaptobenzthiazole;

(3) acylation of the 2′-, 3- and 6′-N positions with an acylating agent;

(4) splitting off of the 2″-O protective group and (5) splitting off of the 1-N-(o-nitrophenylsulphenyl) group.

The starting substances of the formula (III) used as acylating agents can be prepared by processes which are known in principle, by linking an aminoalcohol to the protective group $R_6$ at the amino group and converting the alcoholic group into a reactive carbonate. Examples which may be mentioned are: 4-nitrophenyl 2-trifluoroacetylaminoethyl carbonate, 2,4,5-trichlorophenyl 3-trifluoroacetylaminoprop-1-yl carbonate, 4-nitrophenyl 2-(2-nitrophenylsulphenylamino)-ethyl carbonate, 4-nitrophenyl 6-trifluoroacetylaminohex-1-yl carbonate, 4-nitrophenyl 2-trichloroacetylaminoethyl carbonate, 2,4,5-trichlorophenyl 4-trichloroacetylaminobut-1-yl carbonate, 4-nitrophenyl 2-trichloroacetylaminoprop-1-yl carbonate, 4-nitrophenyl 2-trifluoroacetyl-methylaminoethyl carbonate, 4-nitrophenyl 2-trichloroacetyl-benzylamino-ethyl carbonate and chloroformic acid 2-trichloroacetylaminoethyl ester.

Possible diluents are all the inert organic solvents. These include, preferably, toluene, chloroform, methylene chloride, dimethylformamide, dimethylacetamide, dimethylsulphoxide, ethers, such as diethyl ether, dioxane and tetrahydrofurane, pyridine, alcohols, such as methanol and ethanol, and mixtures thereof.

Suitable bases for the reaction of II with III are all the customary organic and inorganic bases. These include, preferably, alkali metal hydroxides and alkaline earth metal hydroxides, such as sodium hydroxide, potassium hydroxide or calcium hydroxide, alkali metal carbonates and bicarbonates and alkaline earth metal carbonates and bicarbonates, such as sodium carbonate, potassium carbonate, sodium bicarbonate and calcium carbonate, calcium oxide, tertiary aliphatic and aromatic amines particularly those in which the substituent on the nitrogen atoms are alkyl of 1 to 4 carbon atoms, such as triethylamine and N,N-dimethylaniline, and heterocyclic bases, such as pyridine and quinoline.

The reaction temperatures for the reaction of II with III can be varied within a wide range. In general, the reaction is carried out at temperatures from about $-30°$ C. to $+80°$ C., preferably between about $0°$ C. and about $+40°$ C.

The reaction can be carried out under normal pressure, but also under increased pressure. In general, it is carried out under normal pressure.

In carrying out the process according to the invention, 1 mol of the compound of the formula II is reacted with about 1 to 3 mols, preferably with 1.1 to 1.5 mols, of a compound of the formula III. The reaction is preferably carried out in pyridine as the diluent, and at room temperature.

If the protective group $R_6$ is a $-SR_5$ radical, it is in general split off by reaction with nucleophiles, preferably with nucleophiles containing HS groups, such as $H_2S$, thiophenol or 2-mercaptobenzthiazole, at $0°-40°$ C. in a suitable solvent, such as halogenoalkanes, for example methylene chloride, or lower alkanols, for example methanol or ethanol, or in mixtures of such solvents.

If the protective group $R_6$ is a $-COR_4$ radical, it is in general split off under alkaline conditions, for example in the case of the $CF_3CO$—radical, using the bases indicated above as suitable bases for the reaction of II with III, at temperatures of $0°-40°$ C. in polar solvents, such as water, lower alkanols, e.g. having 1 to 4 carbon atoms, such as methanol or ethanol, or mixtures thereof, or under acid conditions, for example in the case of the tert.-butoxycarbonyl radical, using strong acids, such as hydrochloric acid, sulphuric acid or trifluoroacetic acid, under otherwise identical conditions.

The compounds of the formula (I) according to the invention are used as intermediate products for the preparation of highly active 1-N-(ω-aminoalkoxycarbonyl)-sisomicin derivatives, which are obtained if the free amino group in the side chain is alkylated with suitable reagents and the protective groups $R_2$ and $R_3$ are then split off.

Examples of such suitable alkylating reagents are hydroxylated aldehydes or ketones, which, after reductive alkylating linkage with compounds of the formula I and subsequent splitting off of all the protective groups, give 1-N-(hydroxyalkylaminoalkoxycarbonyl)-sisomicins. Compared with other aminoglycoside antibiotics, such as sisomicin, netilmicin or gentamicin, these antibiotics have the advantage of lower toxicity coupled with a high activity, even against resistant bacteria.

EXAMPLE 1

Penta-N-(o-nitrophenylsulphenyl)-2″-O-[dimethyl-(1,2-dimethylpropyl)-silyl]-sisomicin 60.6 g of crude penta-N-(o-nitrophenylsulphenyl)-sisomicin (DE-OS (German Published Specification) No. 2,726,197) and 8.75 g of imidazole are dissolved in 250 ml of absolute methylene chloride. 22.5 ml of dimethyl-(1,2-dimethyl-propyl)-silyl chloride are added dropwise at 0° C., with exclusion of moisture. The batch is evaporated in vacuo to about 170 ml and left to stand at room temperature for 48 hours. After adding 130 ml of absolute methylene chloride, the precipitate is filtered off, the filtrate is thoroughly shaken with 350 ml of petroleum ether and the petroleum ether phase is decanted off and discarded. The oil which has separated out is dissolved in 100 ml of methylene chloride and the product is again separated out with 250 ml of petroleum ether and finally dried under a high vacuum. Yield: 60 g (89%) of crude product, which is employed for the subsequent reactions without further purification. A pure product is obtained by chromatography on silica gel using $CH_2Cl_2/CH_3OH=99/1$.

13-C NMR ($CDCl_3$): δ=124–138 (aromatic C); 147.54 (C-5′); 102.26 (C-1″); 97.81 (C-4′); 99.09 (C-1′); −2.9 to −3.0 (Si—$CH_3$);

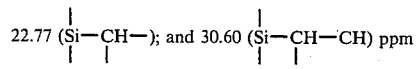

22.77 (Si—CH—); and 30.60 (Si—CH—CH) ppm

Penta-N-(o-nitrophenylsulphenyl)-2″,5-bis—O—[-dimethyl-(1,2-dimethyl-propyl)-silyl]-sisomicin is isolated as a by-product.

13-C-NMR ($CDCl_3$): δ=124–146 (aromatic C), 148.00 (C-5′); and 96.13 (C-4′) ppm

EXAMPLE 2

1,3″-Bis-N-(o-nitrophenylsulphenyl)-2″-O-[dimethyl-(1,2-dimethyl-propyl)-silyl]-sisomicin 16 g of 2-mercapto-benzthiazole are added to 56 g of crude penta-N-(o-nitrophenylsulphenyl)-2″-O-[dimethyl-(1,2-dimethyl-propyl)-silyl]-sisomicin in 36 ml of methylene chloride/70 ml of methanol, the mixture is shaken until a clear solution is formed and the solution is left to stand at 5° C. for 2 hours. The precipitate which thereby separates out is filtered off and the solution is used for the subsequent reactions without isolation of the desired product. The yield is about 80% of theory. To prepare a pure product, the filtrate is evaporated rapidly in vacuo and the residue is chromatographed on silica gel using (a) methylene chloride, (b) methylene chloride/$CH_3OH$ (8:2) and (c) $CH_2Cl_2/CH_3OH/20\%$ strength aqueous ammonia (7:2.7:0.3). The yield of pure product is 25.3 g (69%)

13-C-NMR ($CD_3OD$): δ=1.5 (Si—$CH_3$); 122–146 (aromatic C); 147.14 (C-5′); 103.31 (C-1″); 100.16 (C-1′) and 99.30 (C-4′) ppm 3 g (10%) of 3″-N-(o-nitrophenylsulphenyl)-2″-O-[dimethyl-(1,2-dimethyl-propyl)-silyl]-sisomicin is isolated as a by-product during the column chromatography.

13-C-NMR ($CD_3OD$): δ=76.66 (C-2″); 21.70 (C-6″); 30.40 (N—$CH_3$); 53.13 (C-1), 52.18 (C-3); 44.06 (C-6′) and 49.41 (C-2′) ppm

EXAMPLE 3

1,3″-Bis-N-(o-nitrophenylsulphenyl)-2′,3,6′-tris-N-trichloroacetyl-2″-O-[dimethyl-(1,2-dimethyl-propyl)-silyl]-sisomicin 7.5 ml of trichloroacetic anhydride are added dropwise to 8.8 g of 1,3″-bis-N-(o-nitrophenylsulphenyl)-2″-O-[dimethyl-(1,2-dimethyl-propyl)-silyl]-sisomicin in 20 ml of methylene chloride/20 ml of pyridine at −15° C. and stirring is continued, at room temperature, for another 10 minutes. After adding 20 ml of methylene chloride, the batch is extracted twice by shaking with 20 ml of $H_2O$ each time, the organic phase is evaporated and the residue is further processed as the crude product. $R_F$ ($CH_2Cl_2/CH_3OH=97.5/2.5$)=0.72

EXAMPLE 4

1,3″-Bis-N-(o-nitrophenylsulphenyl)-2′,3,6′-tris-N-trichloroacetyl-sisomicin

The crude oil from Example 3 is dissolved in 20 ml of dimethylsulphoxide, 2 ml of a 50 percent strength KF solution are added and the mixture is stirred vigorously for 3 hours. The product is precipitated with water, washed with water and dried. The crude product is subsequently processed without further purification.

13-C-NMR ($CDCl_3$): δ=103.60 (C-1″); 66.48 (C-3″); 55.15 (C-1); 50.60 (C-3); 79.86 (C-4); 76.18 (C-5); 89.16 (C-6); 97.74 (C-1′); 96.84 (C-4′); 149.80 (C-5); 92.78 ($CCl_3$); 162.29 and 162.11 (CO) ppm.

EXAMPLE 5

3″-N-(o-Nitrophenylsulphenyl)-2′,3,6′-tris-N-trichloroacetyl-sisomicin

The product from Example 4 is dissolved in 13 ml of methylene chloride, the solution is shaken with 26 ml of methanol and 5 g of 2-mercaptobenzthiazole until a clear solution is obtained and this solution is left to stand at 5° C. for 3 days. The precipitate is filtered off, the filtrate is evaporated and the residue is chromatographed on silica gel (running agent a: $CH_2Cl_2/CH_3OH=95/5$; b: /$CH_2Cl_2/CH_3OH/20\%$ strength $NH_3=93/6.5/0.5$).

13-C-NMR ($CDCl_3$): δ=103.43 (C-1″); 67.46 (C-3″); 50.85 (C-1); 50.28 (C-3); 79.44 (C-4); 76.51 (C-5); 89.29 (C-6); 97.61 (C-1′); 96.62 (C-4′); 149.50 (C-5′); 92.46 and 92.38 (C-4′); and 162.01 and 161.76 (CO) ppm.

EXAMPLE 6

4-Nitrophenyl 2-trifluoroacetylaminoethyl carbonate 52.5 g of trifluoroacetic anhydride are added to 30.5 g of 2-aminoethanol in 200 ml of acetonitrile, whilst cooling with ice, the temperature being kept between 5° and 20° C. When the reaction has subsided, the mixture is concentrated and the residue is fractionated. Yield: 37.5 g of 2-(trifluoroacetylamino)-ethanol of boiling point 130°–131° C./11 mm (slowly crystallises completely).

17 g (0.108 mol) of 2-(trifluoroacetylamino)ethanol are dissolved in 210 ml of pyridine, 21 g of chloroformic acid 4-nitrophenyl ester are added and the mixture is left to stand overnight at room temperature. It is then concentrated, the residue is taken up in methylene chloride and the methylene chloride mixture is washed with ice-water and dried with $Na_2SO_4$. After evaporating off the solvent, 33 g of a light-colored oil are obtained.

IR: 1,720 and 1,770/cm. The product contains about 30% of 4-nitrophenol.

EXAMPLE 7

4-Nitrophenyl 3-trifluoroacetylaminopropyl carbonate

The activated carbonate, IR: 1,710 and 1,765/cm, is prepared analogously to Example 6 from 3-(trifluoroacetylamino)-propan-1-ol (boiling point: 120° C./3 mm; IR: 1,710/cm).

EXAMPLE 8

4-Nitrophenyl 6-trifluoroacetylaminohex-1-yl carbonate

The activated carbonate is obtained as the crude product, IR: 1,720 and 1,770/cm, analogously to Example 6 from 6-(trifluoroacetylamino)-hexan-1-ol (boiling point: 150°–154° C./3.5 mm; IR: 1,710/cm).

EXAMPLE 9

4-Nitrophenyl 2-(2-nitrophenylsulphenyl-methyl-amino)ethyl carbonate

A solution of 1.4 g of 2-methylamino-ethanol in 30 ml of dioxane is initially introduced into the reaction vessel, and a solution of 3.8 g of o-nitrophenylsulphenic acid chloride in 10 ml of dioxane, and 8.5 ml of 2 N sodium hydroxide solution are simultaneously added dropwise, whilst maintaining the pH at 8. After stirring the mixture at room temperature for several hours, it is concentrated in vacuo, the residue is taken up in ethyl acetate and the ethyl acetate mixture is washed twice with water, dried with $Na_2SO_4$ and concentrated in vacuo. The oil which remains is chromatographed over 100 g of silica gel using toluene/ethyl acetate (2:1) and the main component ($R_f$: 0.29) is separated off. Yield: 2.9 g of N-(2-hydroxyethyl)-N-methyl-o-nitrosulphenic acid amide; melting point: 53°–56° C.

456 mg of this compound and 600 mg of chloroformic acid p-nitrophenyl ester are dissolved in 5 ml of acetonitrile, and 300 mg of triethylamine in 5 ml of acetonitrile are added, whilst cooling with ice. After 1 hour at room temperature, the mixture is concentrated in vacuo, the residue is taken up in 30 ml of methylene chloride, the methylene chloride mixture is washed twice with water, dried with $Na_2SO_4$ and concentrated in vacuo, the resulting organge oil is chromatographed over 100 g of silica gel using toluene/ethyl acetate (2:1) and the main fraction is separated off. Yield: 250 mg of an orange oil which slowly crystallises completely.

IR (KBr): 1,770 cm$^{-1}$. $R_f$ value (toluene/ethyl acetate 2:1):0.84.

EXAMPLE 10

4-Nitrophenyl 2-(2-nitrophenylsulphenylamino)-ethyl carbonate

The procedure followed is analogous to Example 9; IR: 1,770 cm$^{-1}$; $R_f$ value (toluene/ethyl acetate 2:1):0.77.

EXAMPLE 11

1-N-(2-Aminoethoxycarbonyl)-3,2',6',3''-tetra-N-(o-nitrophenylsulphenyl)-sisomicin 3.3 g of 3,2',6',3''-tetra-N-(o-nitrophenylsulphenyl)-sisomicin (DE-OS (German Published Specification) No. 2,726,197) are dissolved in 15 ml of pyridine, 3.5 g of the product from Example 6 are added, the mixture is stirred at room temperature and the course of the reaction is followed by thin layer chromatography (pre-coated silica gel plates; running agent: methylene chloride/methanol=95/5). After leaving the mixture to stand overnight, it is concentrated under a high vacuum, the residue is taken up in 140 ml of methylene chloride/60 ml of methanol, and 6 ml of 4 N NaOH are added dropwise, whilst stirring. After 1 hour at room temperature, splitting off of the protective groups has ended. The NaOH phase is separated off and the organic phase is washed with water until it no longer gives a basic reaction. After drying with $Na_2SO_4$, the organic phase is evaporated in vacuo and the residue is chromatographed on 200 g of silica gel in order to separate off some non-polar impurities, the column first being eluted with methylene chloride and then with methylene chloride/methanol (5:1).

Yield: 2.2 g of an orange solid product; $R_f$ value (methylene chloride/methanol 5:1): 0.4.

EXAMPLE 12

1-N-(3-Aminopropoxycarbonyl)-3,2',6',3''-tetra-N-(o-nitrophenylsulphenyl)-sisomicin The procedure followed is as according to Example 11, using the activated carbonate from Example 7, and the reaction product is obtained in 55% yield. $R_f$ value (methylene chloride/methanol 5:1):0.42.

EXAMPLE 13

1-N-(6-Aminohexyloxycarbonyl)-3,2',6',3''-tetra-N-(o-nitrophenylsulphenyl)-sisomicin The procedure followed is as according to Example 11, using the carbonate from Example 8, and the sisomicin derivative is obtained in 52% yield. $R_f$ value (methylene chloride/methanol 5:1):0.5.

EXAMPLE 14

1-N-(2-Aminoethoxycarbonyl)-3''-N-(o-nitrophenylsulphenyl)-3,2',6'-tris-N-(trichloroacetyl)-sisomicin 500 mg of the product from Example 10 are added to a solution of 1.04 g of the product from Example 5 in 5 ml of pyridine and the mixture is stirred at room temperature. After 2 hours, starting compound can no longer be detected by thin layer chromatography (pre-coated silica gel plates, running agent=methylene chloride/methanol/20% strength aqueous $NH_3$=930/65/5). The mixture is evaporated under a high vacuum, the residue is taken up in methylene chloride and the methylene chloride mixture is washed with water, dried with $Na_2SO_4$ and concentrated again. To split off the NPS group from the primary amino group, the residue is taken up in 3 ml of methanol/2 ml of methylene chloride, 170 mg of 2-mercaptobenzthiazole are added and the mixture is left to stand at room temperature for 1 day. It is then concentrated and the polar product obtained by splitting off the protective groups is purified by chromatography on 70 g of silica gel (running agent as above) to remove some non-polar components. Yield: 577 mg of an orange solid product. $R_f$ value (running agent as above): 0.15.

EXAMPLE 15

1-N-(2-Methylaminoethoxycarbonyl)-3''-N-(o-nitrophenylsulphenyl)-3,2',6'-tris-N-(trichloroacetyl)-sisomicin The procedure followed is analogous to Example 14 and the sisomicin derivative is obtained in 45% yield. $R_f$ value (methylene chloride/methanol/20% strength $NH_3=930/65/5$):0.17.

EXAMPLE 16

1-N-[2-(1,3-dihydroxypropyl-2-amino)-ethoxycarbonyl]-sisomicin 115 mg of the product from Example 11 are dissolved in 2.5 ml of methanol/0.4 ml of methylene chloride/0.5 ml of water, the solution is adjusted to pH 6 with acetic acid, and 20 mg of dihydroxyacetone are added. The mixture is stirred at room temperature for 15 minutes and 15 mg of $NaBCNH_3$ are then added. After a further 30 minutes, a new product can be detected by thin layer chromatography (thin layer chromatogram:silica gel; methylene chloride/methanol=5:1; $R_f$ value=0.53), and is isolated by adding 5 ml of ethyl acetate, washing the mixture with $2\times5$ ml of water and drying it with $Na_2SO_4$ and concentrating the filtrate in vacuo. The o-nitrophenylsulphenyl protective groups are split off by dissolving the residue in 0.6 ml of methylene chloride, adding 1.6 ml of a solution of 8.5 g of 2-mercaptobenzthiazole in 30 ml of methanol/50 ml of methylene chloride and acidifying the mixture with dilute hydrochloric acid until it becomes light in colour. The sisomicin derivative is extracted, with 1 ml of water, from the solution obtained in splitting off the protective groups and the aqueous phase is washed with $2\times0.5$ ml of methylene chloride and rendered basic with the basic ion exchanger Lewatit MP 500 ($OH^-$). The mixture is evaporated and the residue is chromatographed over 5 g of silica gel using methylene chloride/methanol/20% strength $NH_3$ (2:4:1) as the running agent to remove a small amount of impurities; yield=29 mg $R_f$ value (silica gel, methylene chloride/methanol/concentrated $NH_3=2:2:1$):0.44.

What is claimed is:

1. A compound of the formula I

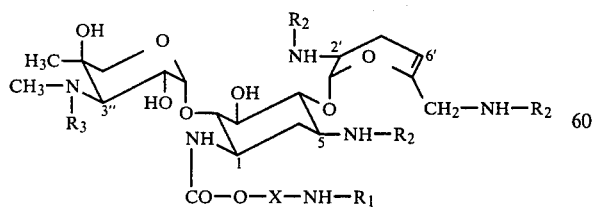

in which
X represents a straight-chain, branched or cyclic saturated or unsaturated aliphatic radical with 2 to 10 C atoms, $R_1$ represents hydrogen, $C_1-C_4$-alkyl or benzyl,
$R_2$ represents $CO-R_4$ or $S-R_5$ and
$R_3$ represents $S-R_5$,
wherein
$R_4$ denotes a radical of the formulae

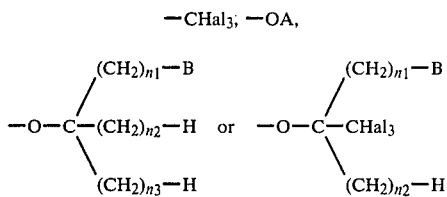

A denotes phenyl which is unsubstituted or substituted by 1 to 3 substituents, said substituents being trifluoromethyl, nitro, $C_1-C_4$-alkyl, $C_1-C_4$-alkoxy, $C_1-C_4$-alkoxycarbonyl and phenyl, or 1 to 5 halogen atoms,
B denotes hydrogen or phenyl which is unsubstituted or substituted by 1 to 3 substituents, said substituents being trifluoromethyl, nitro, $C_1-C_4$-alkyl, $C_1-C_4$-alkoxy, $C_1-C_4$-alkoxycarbonyl and phenyl, or 1 to 5 halogen atoms,
$n_1$, $n_2$ and $n_3$ denote a number from 0 to 5, Hal denotes fluorine, chlorine or bromine and
$R_5$ denotes phenyl or di- or tri-phenylmethyl which is unsubstituted or substituted by 1 to 3 substituents, said substituents being trifluoromethyl, nitro, $C_1-C_4$-alkyl, $C_1-C_4$-alkoxy, $C_1-C_4$-alkoxycarbonyl and phenyl,
or 1 to 5 halogen atoms.

2. A compound according to claim 1, wherein
X denotes $C_2-C_6$-alkylene and
$R_1$ denotes hydrogen.

3. Process for the preparation of a compound according to claim 1, which comprises reacting a compound of the formula

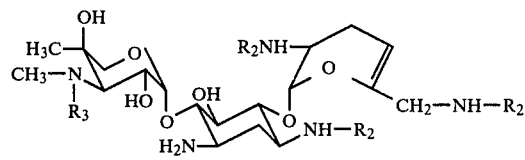

wherein
$R_2$ and $R_3$ have the meaning given in claim 1, with an acylating agent of the formula

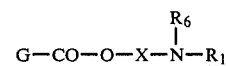

wherein
X and $R_1$ have the meaning given in claim 1,
G represents a leaving group which is halogen, azido, 4-nitrophenoxy, 2,4,5-trichlorophenoxy or

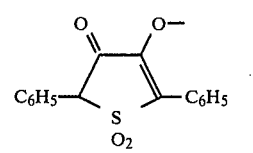

and $R_6$ represents $-COR_4$ or $-SR_5$, wherein
$R_4$ and $R_5$ have the meaning given in claim 1, with the condition that $R_6$ represents $COR_4$ if $R_2$ denotes $SR_5$ and $R_6$ represents $SR_5$ if $R_2$ denotes $COR_4$, and then selectively splitting off the protective group $R_6$ in the presence of the protective groups $R_2$ and $R_3$.